United States Patent

Bhalla et al.

[11] Patent Number: 5,591,693
[45] Date of Patent: Jan. 7, 1997

[54] TURFGRASS MANAGEMENT COMPOSITIONS

[75] Inventors: Prithvi R. Bhalla, East Windsor; Robert M. Herrick, Mercerville, both of N.J.; Donald W. Gates, Yardley, Pa.

[73] Assignee: American Cyanamid Company, Madison, N.J.

[21] Appl. No.: 235,937

[22] Filed: May 2, 1994

Related U.S. Application Data

[62] Division of Ser. No. 833,221, Feb. 10, 1992, Pat. No. 5,340,791, which is a division of Ser. No. 411,444, Sep. 22, 1989, Pat. No. 5,116,403, which is a continuation of Ser. No. 818,591, Jan. 15, 1986, abandoned, which is a continuation-in-part of Ser. No. 698,191, Feb. 4, 1985, abandoned.

[51] Int. Cl.$^6$ .......... H01N 43/42; H01N 43/40; H01N 43/50
[52] U.S. Cl. .......... 504/130; 504/139; 504/149
[58] Field of Search .......... 504/130, 139, 504/149

[56] References Cited

U.S. PATENT DOCUMENTS

| | | | |
|---|---|---|---|
| 3,894,078 | 7/1975 | Fridinger | 71/97 |
| 4,188,487 | 2/1980 | Los | 548/301 |
| 4,269,845 | 5/1981 | Worthington et al. | 424/269 |
| 4,288,242 | 9/1981 | Alt et al. | 71/76 |
| 4,344,788 | 8/1982 | Schneider et al. | 71/76 |
| 4,488,896 | 12/1984 | Lamb et al. | 71/92 |
| 4,608,079 | 8/1986 | Los | 71/92 |
| 4,638,068 | 1/1987 | Los | 546/169 |

FOREIGN PATENT DOCUMENTS

| | | |
|---|---|---|
| 0040050 | 11/1981 | European Pat. Off. . |
| 0041624 | 12/1981 | European Pat. Off. . |
| 0041623 | 12/1981 | European Pat. Off. . |
| 0086402 | 8/1983 | European Pat. Off. . |
| 2011876 | 7/1979 | United Kingdom . |

*Primary Examiner*—Brian M. Burn
*Assistant Examiner*—Brian G. Bembenick
*Attorney, Agent, or Firm*—C. F. Costello, Jr.

[57] ABSTRACT

The present invention relates to chemical compositions comprising imidazolinone compounds that are suitable for use in turfgrass management. The invention also provides methods for altering the growth and reducing mowing frequency, suppressing seed head formation and controlling undesirable vegetation in turfgrass.

16 Claims, No Drawings

TURFGRASS MANAGEMENT COMPOSITIONS

This is a divisional of application Ser. No. 07/833,221 filed on Feb. 10, 1992 (U.S. Pat. No. 5,340,791), which is a divisional of 07/411,444 filed on Sep. 22, 1989 (U.S. Pat. No. 5,116,403) which is a continuation of Ser. No. 06/818,591 filed Jan. 15, 1986 (abandoned) which is a CIP of 06/698,191 filed Feb. 4, 1985 (ABA).

BACKGROUND OF THE INVENTION

Maintenance of lawns, sport fields, playgrounds, parks, golf courses, roadsides and cemeteries represents a growing area of interest. The annual investment in time, labor, chemical treatments, fertilization and equipment for the maintenance of turfgrasses was shown in 1965 to be over 4.2 billion dollars. Additionally, it was shown in 1965 that about 50% of total annual lawn care expenditures was almost equally divided between labor (23.5%) and equipment (26.5%).

Since a significant portion of the investment in turfgrass management is devoted to labor costs, and the cost associated with purchasing, maintaining and operating maintenance equipment, it would be highly desirable to be able to supplement turfgrass management practices with chemical treatments which reduce the maintenance requirements of the grass. The development and use of chemical treatments which retard the growth of grass, and hence the frequency of mowing, reduce and inhibit heading, control undesirable weeds and are not injurious to the grass and do not alter its appearance could significantly reduce the overall maintenance costs for turfgrass management.

Advances in the development of chemical herbicide treatments for the control of weeds have resulted in a wide variety of chemicals which are suitable for weed control in turf. Advances in the field of plant growth regulators have resulted in the discovery that certain of these chemicals are suitable for use on turfgrasses For example, mefluidide, (Embark®) N-[2,4-dimethyl-5-[[(trifluoromethyl)sulfonyl] amino]phenyl]acetamide, a plant growth regulator produced by 3M Company, is registered for use as a growth and development retardant on turf and ornamental species. More recently, work in the area of turfgrass treatment has resulted in the evaluation of mixtures of chemicals in an attempt to enhance effects, improve safety margins, obtain several effects at the same time, reduce rates of application or alter the effect obtained on one specific species.

Certain chemical combinations useful as turfgrass treatments were reported by K. J. Tautvydas in the *Proceedings of Tenth Annual Meeting of the Plant Growth Regulator Society*, 1983. This article discloses synergistic growth retardation of Kentucky bluegrass and johnsongrass with certain mixtures of mefluidide and chlorsulfuron, 2-chloro-N-[(4-methoxy-6-methyl-1,3,5-triazin-2-yl)aminocarbonyl]benzenesulfonamide, and a similar effect on bluegrass, johnsongrass and bermudagrass with certain mixtures of mefluidide and methyl 2-[[[[(4,6-dimethyl-2-pyrimidinyl)amino]carbonyl]amino]sulfonyl]benzoate.

While it is clear that a great deal of research and progress is being made in developing chemical compositions to aid in total turf management programs, it is also becoming clear that, due to variations in climatic conditions and differences in preferred grass varieties within these different growing regions, different treatments will probably be required on a region-to-region and species-to-species basis.

SUMMARY OF THE INVENTION

It is an object of this invention to provide chemical compositions containing certain imidazolinone compounds of the formula (I)

$$R_1 \text{—} \underset{R_2}{\overset{}{\diagdown}} \text{—} CO_2R \quad \text{—} N \text{—} \overset{CH_3}{\underset{}{\diagup}} CH(CH_3)_2 \qquad (I)$$

wherein X is N or $CR_3$; R is hydrogen;

$C_1$–$C_{12}$ alkyl optionally substituted with one of the following groups: $C_1$–$C_4$ alkoxy, halogen, hydroxyl, $C_3$–$C_6$ cycloalkyl, benzyloxy, furyl, phenyl, halophenyl, $C_1$–$C_4$ alkylphenyl, $C_1$–$C_4$ alkoxyphenyl, nitrophenyl, carboxyl, $C_1$–$C_3$ alkoxycarbonyl, cyano, or tri($C_1$–$C_3$)alkylammonium;

$C_3$–$C_{12}$ alkenyl optionally substituted with one of the following groups: $C_1$–$C_3$ alkoxy, phenyl, halogen, or $C_1$–$C_3$ alkoxycarbonyl or with two $C_1$–$C_4$ alkoxy groups or two halogen atoms;

$C_3$–$C_6$ cycloalkyl optionally substituted with one or two $C_1$–$C_3$ alkyl groups;

$C_3$–$C_{10}$ alkynyl; or a cation;

$R_1$ and $R_2$ are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2CHF_2$, $OCF_3$, $OCHF_2$, nitro, cyano, $C_1$–$C_4$ alkylsulfonyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen;

$R_3$ is hydrogen, halogen, $C_1$–$C_4$ alkyl, $C_1$–$C_4$ alkylthio, $C_1$–$C_4$ alkoxy, $CF_3$, $NO_2$, $OCF_3$, $OCHF_2$, or $OCF_2CHF_2$;

$R_4$ is hydrogen or $C_1$–$C_4$ alkyl;

$R_5$ is $C_1$–$C_4$ alkyl;

and, when taken together, $R_1$ and $R_2$, in the case of $X=CR_3$, may form a ring in which $R_1R_2$ is represented by (1) the structure: $-(CH_2)_n-$, where n is an integer of 2, 3 or 4; or (2) by the structure:

$$-\underset{L}{C}=\underset{M}{C}-\underset{R_6}{C}=\underset{R_7}{C}-$$

where L, M, $R_6$ and $R_7$ each represent hydrogen, halogen, $C_1$–$C_4$ alkyl or $C_1$–$C_3$ alkoxy;

and, in the case of X=N, $R_1$ and $R_2$ (1) may form a ring in which $R_1R_2$ is represented by the structure $-(CH_2)_n-$, where n is an integer of 3 or 4; or (2) when taken together with the carbons to which they are attached may form a 5-membered ring containing one O or S; or (3) may form a ring represented by the structure:

$$-\underset{L}{C}=\underset{M}{C}-\underset{R_6}{C}=\underset{R_7}{C}-$$

where L, M, $R_6$ and $R_7$ each represent hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $C_1$–$C_4$ alkylamino, diloweralkylamino, chlorophenyl, methylphenyl, phenoxy substituted with one $C_1$, $CF_3$, $NO_2$, or $CH_3$ group, $OCF_2CHF_2$, $OCF_3$, $OCHF_2$, $C_3$–$C_8$ straight or branched alkenyloxy optionally substituted with one to three halogens, or $C_3$–$C_8$ straight or branched alkynyloxy optionally substituted with one to three halogens; and the N-oxides thereof when X=N, provided that R cannot be alkenyl or alkynyl and $R_1$ and $R_2$ cannot be $NR_4R_5$ or alkylthio, and the optical isomers thereof and mixtures of regio isomers thereof, alone and in combination with 2-(4-isopropyl-4-methyl-5-oxo-2-imidazolin-2-yl)nicotinic acid or salts thereof, maleic hydrazide, N-[2,4-dimethyl-5-[[(trifluoromethyl)sulfonyl]amino]phenyl]acetamide, 2-chloro-N-[(4-methoxy-6-methyl-1,3,5-triazin-2-yl )aminocarbonyl]benzenesulfonamide or methyl 2-[[[[(4,6-dimethyl-2-pyrimidinyl)amino]carbonyl]amino]sulfonyl]benzoate and mixtures thereof, which provide compositions that reduce growth in a variety of grass species, without being injurious, inhibit seed heading, and control certain weeds, and further that the desired effect or group of effects for a given variety of grass under specific growing conditions may be obtained by altering the combination and rate of each component.

The imidazolinone compounds suitable for use in turf described in U.S. Pat. No. 4,188,487, pending applications for U.S. letters patent Ser. No. 382,041 (U.S. Pat. No. 4,638,068), U.S. Ser. No. 616,747 (abandoned), U.S. Ser. No. 631,283 (U.S. Pat. No. 4,554,013), U.S. Ser. No. 611, 191 (abandoned) and pending application for U.S. letters patent, Ser. No. 635,787 (abandoned) as herbicides and plant growth regulators for increasing crop yields. Surprisingly, it has been found that compounds represented by Formula (I) are efficacious for retarding the growth of turf and suppressing seed heads. Additionally, it has been found that the longevity of the effect and the extent of the effect may be increased significantly by applying formula (I) compounds in combination with one or more of 2-(4-isopropyl-4-methyl-5-oxo-2-imidazolin-2-yl)nicotinic acid or salts thereof, maleic hydrazide, N-[2,4-dimethyl-5-[[(trifluoromethyl)sulfonyl]amino]phenyl]acetamide, 2-chloro-N-[(4-methoxy-6-methyl-1,3,5-triazin-2-yl)aminocarbonyl]benzenesulfonamide and methyl 2-[[[[(4,6-dimethyl-2-pyrimidinyl)amino]carbonyl]amino]sulfonyl]benzoate. Further, it has been found that by altering the rates of each of the components, the desirable effects of growth retardation, head inhibition and control of certain weeds may be obtained in a variety of grass species without being injurious to the grass. Preferred compounds suitable for use in turfgrass management compositions of the invention are illustrated in Table I below.

TABLE I

| Component | | | | |
|---|---|---|---|---|
| 1 | (structure: $R_1$, $R_2$ substituted ring with X, $CO_2R$, and N—CH($CH_3$)$_2$ / N=O / NH—$CH_3$ imidazolinone group) | | | |
| | | X | R | $R_1$ | $R_2$ |
| (a) | | N | H | H | $OCH_3$ |
| (b) | | N | H | —CH=CH—CH=CH— | |
| (c) | | CH / CH | $CH^3$ / $CH_3$ | $CH^3$ / H | H / $CH_3$ |
| (d) | | N | H | —$OCH_2$CH=$CH_2$ | H |
| (e) | | N | H | —$CH_2$—$CH_2$—O— | |
| (f) | | N | $C_2H_5$ | $OCH_3$ | H |
| (g) | | N | H | —C=CH—CH=C— / $OCH_3$ ... $OCH_3$ | |
| (h) | | N | H | $C_2H_5$ | H |
| (i) | | N | H | -phenyl | H |
| (j) | | N | H | —CH=CH—C=CH— / Cl | |
| (k) | | N | $CH_3$ | H | $OCH_3$ |
| 2 | 2-(4-isopropyl-4-methyl-5-oxo-2-imidazolin-2-yl)nicotinic acid | | | | |
| 3 | maleic hydrazide | | | | |
| 4 | N-[¹2,4-dimethyl-5-[[(trifluoromethyl)sulfonyl]amino]phenyl]acetamide | | | | |
| 5 | chlorsulfuron, 2-chloro-N-[(4-methoxy-6-methyl-1,3,5-triazin-2-yl)aminocarbonyl]benzenesulfonamide | | | | |
| 6 | methyl 2-[[[[(4,6-dimethyl-2-pyrimidinyl)amino]carbonyl]amino]sulfonyl]benzoate | | | | |

As indicated above, the composition of the invention may be altered to obtain different effects or the same set of effects on a different grass species without injuring the grass. The preferred ranges of rates for each of the components are illustrated in Table II below.

TABLE II

Preferred rate ranges for turf management compositions of the invention

| Composition | Rate grams/hectare |
|---|---|
| 1 | 5 to 500 |
| 2 | 0.1 to 200 |
| 1 + 2 | 5 to 250 + 0.25 to 25 |
| 1 + 3 | 5 to 250 + 20 to 5000 |
| 1 + 4 | 5 to 250 + 20 to 500 |
| 1 + 5 | 5 to 250 + 0.25 to 20 |
| 1 + 6 | 5 to 250 + 0.25 to 20 |
| 1 + 2 + 4 | 1 to 250 + 0.25 to 25 + 20 to 500 |
| 1 + 2 + 5 | 1 to 250 + 0.25 to 25 + 0.25 to 20 |
| 1 + 2 + 6 | 1 to 250 + 0.25 to 25 + 0.25 to 20 |

As discussed above, by adjusting the rates of each component the compositions may be used on a variety of species as indicated in Table III below.

TABLE III

Adjusting Composition for different grass species

| Composition | Bermudagrass | Bluegrass | Fescue | Rye |
|---|---|---|---|---|
| 1 | 5.0 to 500.0* | 5.0 to 500.0 | 5.0 to 250.0 | 5.0 to 250.0 |
| 2 | 5.0 to 200.0 | 0.1 to 20.0 | 0.1 to 10.0 | 0.1 to 10.0 |
| 1 + 2 | 5.0 to 250.0 + 0.25 to 25.0 | 5.0 to 250.0 + 0.25 to 25.0 | 5.0 to 150.0 + 0.5 to 10.0 | 5.0 to 150.0 + 0.5 to 10.0 |
| 1 + 3 | 5.0 to 250.0 + 20.0 to 5000.0 | 5.0 to 250.0 + 20.0 to 5000.0 | 5.0 to 150.0 + 20.0 to 2500.0 | 5.0 to 150.0 to 20.0 to 2500.0 |
| 1 + 4 | 50.0 to 250.0 + 0.25 to 10.0 | 5.0 to 250.0 + 0.25 to 10.0 | 5.0 to 150.0 + 0.25 to 5.0 | 5.0 to 150.0 + 0.25 to 5.0 |
| 1 + 5 | 5.0 to 250.0 + 0.25 to 10.0 | 5.0 to 250.0 + 0.25 to 10.0 | 5.0 to 150.0 + 0.25 to 5.0 | 5.0 to 150.0 + 0.25 to 5.0 |
| 1 + 6 | 5.0 to 250.0 + 0.25 to 10.0 | 5.0 to 250.0 + 0.25 to 10.0 | 5.0 to 150.0 + 0.25 to 5.0 | 5.0 to 150.0 + 0.25 to 5.0 |
| 1 + 2 + 4 | 1 to 250 + 0.25 to 25 + 20 to 500 | 1 to 250 + 0.25 to 25 + 20 to 500 | 1 to 250 + 0.25 to 10 + 20 to 500 | 1 to 250 + 0.25 to 10 + 20 to 250 |
| 1 + 2 + 5 | 1 to 250 + 0.25 to 25 + 0.25 to 10 | 1 to 250 + 0.25 to 25 + 0.25 to 10 | 1 to 250+ 0.25 to 25 + 0.25 to 5 | 1 to 250 + 0.25 to 25 + 0.25 to 5 |
| 1 + 2 + 6 | 1 to 250 + 0.25 to 25 + 0.25 to 10 | 1 to 250 + 0.25 to 25 + 0.25 to 10 | 1 to 250 + 0.25 to 25 + 25 + 0.25 to 5 | 1 to 250 + 0.25 to 25 + 0.25 to 5 |

*Rate in grams/hectare

The compositions of the invention may conveniently be applied by post-emergence treatment of the grass. They may be applied as a mixture of all the ingredients or as sequential treatments. Since the formula (I) compounds wherein R is hydrogen are acids, as is 2-(4-isopropyl-4-methyl-5-oxo-2-imidazolin-2-yl)nicotinic acid and these compounds may be applied as salts of the acid wherein R is a salt-forming cation, the compositions may be applied as aqueous solutions and suspensions containing non-ionic surfactants, and wetting agents which may be prepared by introducing the components directly to water or by adding formulations such as concentrates, suspensions, emulsions, wettable powders, dispersible granules and the like to water prior to application. Additionally granular compositions containing some of the compositions of the invention may be applied to the turf followed by additional post-emergence treatments as required. The invention is further illustrated by the following non-limiting examples.

EXAMPLE 1

Evaluation of compositions of the invention for retarding growth

Seeds of the grass variety to be evaluated are tumbled for three minutes with soil at a rate of 7 ounces of seed per 100 lbs of greenhouse soil, comprising a mixture by weight of sand (32%), silt (48%), and clay (20%). A layer of this seed mixture one-half inch thick is placed in a four inch diameter pot containing greenhouse soil and the plants are allowed to germinate and grow for six to eight weeks prior to treatment. The plants are clipped to a height of one-half inch and are sprayed with 100 mL of an aqueous solution containing 0.25% by volume of a nonionic surfactant mixture alkylarylpolyoxyethyleneglycols, free fatty acids and 2-propanol, and the formula I (a)-(k) compounds and compounds 2, 3, 4, and 5 both alone and in combinations at various spray rates. Each treatment is applied to three pots and the pot randomly placed in a greenhouse where the plants are cared for employing standard greenhouse procedures. Three weeks after treatment the plants are clipped to a height of one-half inch and the clippings are dried in an oven for 48 hours at 90° C. and the dry weight of clippings for each treatment is recorded. Examination of Tables IV and V below which is a summary of results obtained on tall fescue and bermudagrass, respectively, clearly demonstrates the effectiveness of the formula I (a)-(k) compounds alone and additionally demonstrates the improved effectiveness of these formula I (a)-(k) compounds in combination with compounds 2, 3, 4 and 5 for retarding the growth of turfgrasses as measured by dry clipping weight.

TABLE IV

Greenhouse evaluation of compositions of the invention on tall fescue (*Festuca arundinaceae*)

| Treatments | Rate(s) g or lb/A | % Decrease in dry wt of clipping |
|---|---|---|
| 1(h) | 20.0 g | 37 |
| 1(h) | 40.0 g | 51 |
| 2 | 1.0 g | 2 |
| 2 | 2.0 g | 3 |
| 1(j) | 20.0 g | 29 |
| 1(j) | 40.0 g | 32 |
| 1(j) | 60.0 g | 25 |
| 1(h) + 2 | 20.0 g + 1.0 g | 52 |
| 1(h) + 2 | 20.0 g + 2.0 g | 52 |
| 1(h) + 2 | 40.0 g + 1.0 g | 37 |
| 1(h) + 2 | 40.0 g + 2.0 g | 76 |
| 4 | 0.125 lb | 6 |
| 4 | 0.375 lb | 59 |
| 1(h) + 4 | 20.0 g + 0.125 lb | 80 |
| 1(j) + 4 | 40.0 g + 0.125 lb | 82 |
| 1(j) + 4 | 20.0 g + 0.125 lb | 60 |
| 1(j) + 4 | 40.0 g + 0.125 lb | 46 |
| 1(j) + 4 | 60.0 g + 0.125 lb | 64 |
| 3 | 1.5 lb | 2 |
| 3 | 3.0 lb | 7 |
| 1(h) + 3 | 20.0 g + 1.5 lb | 45 |
| 1(h) + 3 | 40.0 g + 1.5 lb | 66 |
| 1(j) + 3 | 20.0 g + 1.5 lb | 70 |
| 1(j) + 3 | 20.0 g + 1.5 lb | 70 |
| 1(j) + 3 | 40.0 g + 1.5 lb | 49 |
| 1(j) + 3 | 60.0 g + 1.5 lb | 46 |

TABLE V

Greenhouse evaluation of compositions of the invention on burmudagrass (*Cynodon sp*)

| Treatments | Rates (grams/Acre) | % Decrease in dry wt of clippings |
|---|---|---|
| 1(h) | 5.0 | 15.3 |
| 1(h) | 10.0 | 14.7 |
| 1(h) | 15.0 | 12.7 |
| 1(h) | 20.0 | 12.7 |
| 1(h) | 40.0 | 57.3 |
| 1(h) | 100.0 | 71.3 |
| 2 | 2.00 | 24.7 Increase |
| 2 | 4.00 | 8.0 Increase |
| 2 | 6.00 | 59.3 |
| 2 | 8.00 | 82.0 |
| 1(h) + 2 | 5.0 + 2.0 | 19.3 |
| 1(h) + 2 | 5.0 + 4.0 | 44.7 |
| 1(h) + 2 | 5.0 + 8.0 | 82.0 |
| 1(h) + 2 | 10.0 + 0.5 | 34.0 |
| 1(h) + 2 | 10.0 + 1.0 | 5.3 |
| 1(h) + 2 | 10.0 + 2.0 | 38.7 |
| 1(h) + 2 | 10.0 + 4.0 | 52.0 |
| 1(h) + 2 | 10.0 + 6.0 | 86.0 |
| 1(h) + 2 | 10.0 + 8.0 | 86.7 |
| 1(h) + 2 | 15.0 + 0.25 | 38.7 |
| 1(h) + 2 | 15.0 + 0.5 | 18.7 |
| 1(h) + 2 | 15.0 + 1.0 | 2.0 Increase |
| 1(h) + 2 | 15.0 + 2.0 | 8.0 Increase |
| 1(h) + 2 | 15.0 + 4.0 | 10.7 |
| 1(h) + 2 | 15.0 + 6.0 | 83.3 |
| 1(h) + 2 | 15.0 + 8.0 | 78.0 |
| 1(h) + 2 | 20.0 + 0.25 | 48.7 |
| 1(h) + 2 | 20.0 + 0.5 | 16.7 |
| 1(h) + 2 | 20.0 + 1.0 | 18.0 |
| 1(h) + 2 | 20.0 + 2.0 | 54.0 |
| 1(h) + 2 | 20.0 + 4.0 | 45.3 |
| 1(h) + 2 | 20.0 + 6.0 | 66.7 |
| 1(h) + 2 | 25.0 + 0.25 | 7.3 |
| 1(h) + 2 | 25.0 + 0.50 | 27.3 |
| 1(h) + 2 | 25.0 + 1.0 | 36.7 |
| 1(h) + 2 | 25.0 + 2.0 | 75.3 |
| 1(h) + 2 | 25.0 + 4.0 | 76.0 |
| 1(h) + 2 | 30.0 + 6.0 | 88.0 |
| 1(h) + 2 | 30.0 + 0.25 | 36.7 |
| 1(h) + 2 | 30.0 + 0.50 | 20.0 |
| 1(h) + 2 | 30.0 + 1.0 | 42.7 |
| 1(h) + 2 | 30.0 + 2.0 | 78.0 |
| 1(h) + 2 | 30.0 + 4.0 | 64.7 |
| 1(h) + 2 | 30.0 + 0.25 | 16.0 |
| 1(h) + 2 | 35.0 + 0.50 | 44.0 |
| 1(h) + 2 | 35.0 + 1.0 | 31.3 |
| 1(h) + 2 | 35.0 + 2.0 | 58.7 |
| 1(h) + 2 | 40.0 + 0.25 | 48.0 |
| 1(h) + 2 | 40.0 + 0.50 | 32.7 |
| 1(h) + 2 | 40.0 + 1.0 | 42.0 |
| 1(h) + 2 | 40.0 + 2.0 | 68.0 |
| 4 | 50.0 | 5.3 |
| 4 | 100.0 | 5.3 Increase |
| 4 | 500.0 | 48.0 |
| 1(h) + 4 | 10.0 + 50.0 | 35.3 |
| 1(h) + 4 | 10.0 + 100.0 | 27.3 |
| 1(h) + 4 | 10.0 + 500.0 | 47.3 |
| 1(h) + 4 | 15.0 + 50.0 | 12.0 |
| 1(h) + 4 | 15.0 + 100.0 | 4.0 |
| 1(h) + 4 | 15.0 + 500.0 | 17.3 |
| 1(h) + 4 | 20.0 + 50.0 | 29.3 |
| 1(h) + 4 | 20.0 + 100.0 | 34.0 |
| 1(h) + 4 | 20.0 + 500.0 | 50.0 |
| 1(h) + 4 | 25.0 + 50.0 | 54.0 |
| 1(h) + 4 | 25.0 + 100.0 | 63.3 |
| 1(h) + 4 | 25.0 + 500.0 | 12.0 |
| 2 + 4 | 0.5 + 50.0 | 9.3 Increase |
| 2 + 4 | 0.5 + 100.0 | 18.0 Increase |
| 2 + 4 | 0.5 + 500.0 | 36.7 |
| 2 + 4 | 1.0 + 50.0 | 33.3 |
| 2 + 4 | 1.0 + 100.0 | 42.0 |
| 2 + 4 | 1.0 + 500.0 | 48.0 |
| 2 + 4 | 2.0 + 50.0 | 26.7 |
| 2 + 4 | 2.0 + 100.0 | 48.0 |
| 2 + 4 | 2.0 + 500.0 | 75.3 |
| 2 + 4 | 4.0 + 50.0 | 37.3 |
| 2 + 4 | 4.0 + 100.0 | 20.7 |
| 2 + 4 | 4.0 + 500.0 | 33.3 |

EXAMPLE 2

Evaluation of compositions of the invention on a mix stand of grasses which include tall rescue (*Festuca arundinaecae*); Kentucky bluegrass (*Poa pratensis*), annual ryegrass (*Lolium multiforum*) and perennial ryegrass (*Lolium perenne*)

A six foot by twenty foot plot containing a mixed stand of grasses which include tall rescue (*Festuca arundinaecae*); Kentucky bluegrass (*Poa pratensis*), annual ryegrass (*Lolium multiforum*) and perennial ryegrass (*Lolium perenne*) is mowed at a height of one and one-half inches. Twenty-four hours after mowing the plot is sprayed with an aqueous solution containing 0.25% by volume of a nonionic surfactant mixture of alkylarylpolyoxyethyleneglycols, free fatty acids, and 2-propanol and formula I (a)-(k) compounds and compounds 2, 3, 4 and 5 alone and in combinations at a variety of concentrations. Sufficient aqueous solution is applied to provide the equivalent of 25 gal/acre of spray. Each treatment is applied to three plots which are situated randomly within the test area and the results for each treatment are obtained by averaging the three replicates. The height of each treatment plot is measured at three weeks and five weeks after treatment to determine the effectiveness of The treatment in retarding growth. Examination of Table VI below which is a summary of the results obtained on the mixed stand of grasses demonstrates the effectiveness of The formula I (a)-(k) compounds alone and additionally demonstrates the improved effectiveness of these formula I (a)-(k) compounds in combination with compounds 2, 3, 4 and 5 for retarding the growth of turfgrasses.

TABLE VI

Evaluation of compositions of the invention on a mix stand of grasses which include Tall Fescue (*Festuca arundinaecae*), Kentucky Bluegrass (*Poa pratensis*), Annual Ryegrass (*Lolium multiforum*) and Perennial Ryegrass (*Lolium perenne*)

| Treatments | Rate(s) g or lb/A | % Decrease in height 22–25 DAT* | 36–38 DAT* |
|---|---|---|---|
| 1(h) | 25.0 g | 16 | — |
| 1(h) | 50.0 g | 24 | — |
| 1(h) | 75.0 g | 10 | — |
| 1(b) | 1.0 g | 14 | — |
| 1(b) | 2.0 g | 30 | 19 |
| 1(b) | 2.5 g | — | — |
| 1(b) | 5.0 g | — | — |
| 1(d) | 25.0 g | 10 | — |
| 1(d) | 50.0 g | 14 | — |
| 1(d) | 75.0 g | 23 | — |
| 1(a) | 20.0 g | 38 | 37 |
| 1(a) | 40.0 g | 42 | 40 |

TABLE VI-continued

Evaluation of compositions of the invention on a mix stand of grasses which include Tall Fescue (*Festuca arundinaecae*), Kentucky Bluegrass (*Poa pratensis*), Annual Ryegrass (*Lolium multiforum*) and Perennial Ryegrass (*Lolium perenne*)

| Treatments | Rate(s) g or lb/A | % Decrease in height 22–25 DAT* | 36–38 DAT* |
|---|---|---|---|
| 1(a) | 60.0 g | 37 | 34 |
| 3 | 5.0 lb | 14 | — |
| 5 | 3.5 g | 8 | — |
| 5 | 7.0 g | 4 | — |
| 4 | 0.5 lb | 23 | 8 |
| 1(h) + 1(b) | 25.0 g + 2.5 g | — | — |
| 1(h) + 1(b) | 25.0 g + 5.0 g | 15 | — |
| 1(h) + 2 | 25.0 g + 1.0 g | 28 | — |
| 1(h) + 2 | 25.0 g + 2.0 g | 29 | — |
| 1(h) + 2 | 50.0 g + 1.0 g | — | 10 |
| 1(h) + 2 | 50.0 g + 2.0 g | 26 | 12 |
| 1(d) + 2 | 25.0 g + 1.0 g | 23 | — |
| 1(d) + 2 | 25.0 g + 2.0 g | 11 | — |
| 1(h) + 3 | 25.0 g + 1.5 lb | 16 | 13 |
| 1(h) + 3 | 50.0 g + 1.5 lb | 29 | 12 |
| 1(h) + 4 | 25.0 g + 0.125 lb | 42 | 16 |
| 1(h) + 4 | 50.0 g + 0.125 lb | 38 | 27 |
| 1(h) + 5 | 20.0 g + 3.5 g | 16 | — |
| 1(d) + 4 | 25.0 g + 0.125 lb | 37 | 13 |
| 1(d) + 5 | 25.0 g + 3.5 g | 19 | 13 |
| 1(d) + 3 | 25.0 g + 1.5 lb | 31 | 13 |
| 1(d) + 3 | 50.0 g + 1.5 lb | 29 | 14 |
| 1(k) | 20.0 g | 27 | — |
| 1(k) | 40.0 | 29 | 11 |
| 1(k) | 60.0 g | 24 | 31 |
| 1(k) | 80.0 g | 37 | 41 |
| 1(d) | 20.0 g | 22 | — |
| 1(d) | 40.0 g | 24 | — |
| 1(d) | 60.0 g | 19 | — |
| 1(d) | 80.0 g | 35 | 23 |
| 2 | 1.0 g | — | — |
| 2 | 2.0 g | — | 7.2 |
| 1(k) + 2 | 20.0 g + 1.0 g | 21 | 16 |
| 1(k) + 2 | 20.0 g + 2.0 g | 28 | 25 |
| 1(k) + 2 | 40.0 g + 1.0 g | 22 | 34 |
| 1(k) + 2 | 40.0 g + 2.0 g | 32 | 30 |
| 1(d) + 2 | 20.0 g + 1.0 g | 16 | — |
| 1(d) + 2 | 20.0 g + 2.0 g | 19 | 13 |
| 1(d) + 2 | 40.0 g + 1.0 g | 19 | — |
| 1(d) + 2 | 40.0 g + 2.0 g | 26 | 29 |
| 4 | 0.125 lb | 26 | 29 |
| 4 | 0.375 lb | 15 | 19 |
| 4 + 2 | 0.125 lb + 1 g | 34 | 29 |
| 4 + 2 | 0.125 lb + 2 g | 38 | 25 |
| 4 + 1(k) | 0.125 lb + 20 g | 31 | 23 |
| 4 + 1(d) | 0.125 lb + 20 g | 29 | 13.5 |
| 5 | 2.0 g | — | — |
| 5 | 7.0 g | 15 | — |
| 5 + 2 | 2.0 g + 1.0 g | 21 | 4 |
| 5 + 4 + 2 | 2.0 g + 0.125 g + 1.0 g | 28 | 5.8 |
| 5 + 4 + 1(d) | 2.0 g + 0.125 g + 20.0 g | 27 | — |
| 5 + 4 + 1(k) | 2.0 g + 0.125 g + 20.0 g | 44 | 10 |

*DAT = Days after treatment

EXAMPLE 3

Evaluation of 2-(4-isopropyl-4-methyl-5-oxo-2-imidazolin-2-yl)-5-methyl-nicotinic acid for retarding growth of turfgrasses An evaluation of another composition of the invention is conducted using the procedure of Example 1 above and Bermudagrass (*Cynodon doctylon*) as the turfgrass species.

The test composition, 2-(4-isopropyl-4-methyl-5-oxo-2-imidazolin-yl)-5-methyl-nicotinic acid, is applied to said turfgrass at rates of from 25 to 200 grams per hectare. Test compound is applied in the form of an aqueous solution as described in Example 1 and treated plants were held in the greenhouse for 60 days after treatment and then harvested.

Data obtained are reported in Table VII below.

TABLE VII

| Rate (g/ha) | Phytotoxicity Rating** | Clipping* Fresh Weight (g) | Clipping* Dry Weight (g) |
|---|---|---|---|
| 0 | 0 | 369 | 97 |
| 25 | 0 | 231 (37.4%) | 59 (39.1%) |
| 50 | 0 | 209 (43.3%) | 54 (44.3%) |
| 100 | 1 | 163 (55.8%) | 41 (57.7%) |
| 150 | 3 | 114 (69.1%) | 30 (69.0%) |
| 200 | 5 | 68 (81.5%) | 23 (76.2%) |

*% Reduction over checks is shown in parenthesis.
**Phytotoxicity Rating ranges from 0 meaning no injury to 10 meaning complete kill.

What is claimed is:

1. A composition for retarding growth and suppressing seed heading in turfgrasses, comprising a synergistic effective amount of at least one compound having the structure:

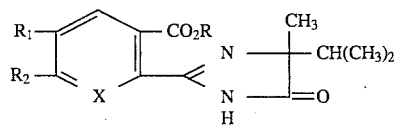

wherein X is N or CH; R is H, $C_1$–$C_4$ alkyl, or a cation; $R_1$ and $R_2$ are each H, $C_1$–$C_4$ alkyl, $C_1$–$C_4$ alkyloxy, $C_3$–$C_6$ alkenyloxy, or $R_1$ and $R_2$ taken together with the carbons to which they are attached may form a 6 membered ring; and the optical isomer thereof, in combination with N-[2,4-dimethyl-5[[(trifluoromethyl)-sulfonyl]amino]phenyl]acetamide.

2. A composition according to claim 1, comprising a mixture of 2-(4-isopropyl-4-methyl-5-oxo-2-imidazolin-2-yl) 3-quinolinecarboxylic acid and N-[2,4dimethyl-5-[[(trifluoromethyl)sulfonyl]amino]phenyl]acetamide.

3. A composition according to claim 1, comprising a mixture of 5-ethyl-2-(4-isopropyl-4-methyl-5-oxo-2-imidazolin-2-yl)nicotinic acid and N-[2,4-dimethyl-5-[[(trifluoromethyl)sulfonyl]amino]phenyl]acetamide.

4. A composition according to claim 1, comprising a mixture of methyl 6-(5-isopropyl-5-methyl-4-oxo-2-imidazolin-2-yl) m-toluate and methyl 2-(5-isopropyl-5-methyl-4-oxo-2-imidazolin-2-yl) p-toluate and N-[2,4-dimethyl-5-[[(trifluoromethyl)sulfonyl]amino]phenyl]acetamide.

5. A composition according to claim 1, comprising a mixture of methyl 2-(4-isopropyl-4-methyl-5-oxo-2-imidazolin-2-yl)-6-methoxy nicotinate and N-[2,4-dimethyl-5-[[(trifluoromethyl)sulfonyl]amino]phenyl]acetamide.

6. A composition according to claim 1, comprising a mixture of 5-(allyloxy)-2-(4-isopropyl-4-methyl-5-oxo-2-imidazolin-2-yl)nicotinic acid and N-[2,4-dimethyl-5-[[(trifluoromethyl)sulfonyl]amino]phenyl]acetamide.

7. A composition according to claim 1, comprising 2-(4-isopropyl-4-methyl-5-oxo-2-imidazolin-2-yl)nicotinic acid or salts thereof and N-[2,4-dimethyl-5-[[(trifluoromethyl)sulfonyl]amino]phenyl]acetamide.

8. A method for retarding growth and suppressing seed-heading in turfgrasses, which comprises applying to the foliage or soil surrounding the turfgrasses, a sufficient quantity of a composition having a synergistic effective amount of at least one compound comprising the structure:

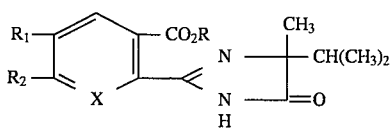

wherein X is N or CH; R is H, $C_1$–$C_4$ alkyl, or a cation; $R_1$ and $R_2$ are each H, $C_1$–$C_4$ alkyl, $C_1$–$C_4$ alkyloxy, $C_3$–$C_6$ alkenyloxy, or $R_1$ and $R_2$ taken together with the carbons to which they are attached may form a 6 membered ring: and the optical isomer thereof, in combination with N-[2,4-dimethyl-5[[(trifluoromethyl)-sulfonyl]amino]phenyl]acetamide.

9. A method according to claim 8, comprising applying to turfgrasses a mixture of 2-(4-isopropyl-4-methyl-5-oxo-2-imidazolin-2-yl) 3-quinolinecarboxylic acid and N-[2,4-dimethyl-5-[[(trifluoromethyl)sulfonyl]amino]phenyl]acetamide.

10. A method according to claim 8, comprising applying to turfgrasses a mixture of 5-ethyl-2-(4- isopropyl-4-methyl-5-oxo-2-imidazolin-2-yl )nicotinic acid and N-[2,4-dimethyl-5-[[(trifluoromethyl)sulfonyl]amino]phenyl]acetamide.

11. A method according to claim 8, comprising applying to turfgrasses a mixture of methyl 6-(5-isopropyl-5-methyl-4-oxo-2-imidazolin-2-yl) m-toluate and methyl 2-(5-isopropyl-5-methyl-4-oxo-2-imidazolin-2-yl) p-toluate and N-[2,4-dimethyl-5[[(trifluoromethyl)sulfonyl]amino]phenyl]acetamide.

12. A method according to claim 8, comprising applying to turfgrasses a mixture of methyl 2- (4-isopropyl-4-methyl-5-oxo-2-imidazolin-2-yl)-6-methoxy nicotinate and N-[2,4-dimethyl-5-[[(trifluoromethyl)sulfonyl]amino]phenyl]acetamide.

13. A method according to claim 8, comprising applying to turfgrasses a mixture of 5-(allyl-oxy)-2-(4-isopropyl-4-methyl-5-oxo-2-imidazolin-2-yl)nicotinic acid and N-[2,4-dimethyl-5-[[(trifluoromethyl)sulfonyl]amino]phenyl]acetamide.

14. A method according to claim 8, comprising applying to turfgrasses a mixture of 2-(4-isopropyl-4-methyl-5-oxo-2- imidazol in-2-yl )nicotinic acid or salt thereof and N-[2, 4-dimethyl-5-[[(trifluoromethyl)sulfonyl]amino]phenyl]acetamide.

15. A method according to claim 8, wherein the formula I compound is 2-(4-isopropyl-4-methyl-5-oxo-2-imidazolin-2-yl)-5-methyl-nicotinic acid or salt thereof.

16. A method according to claim 8, wherein the formula I compound is 2-(4-isopropyl-4-methyl-5-oxo-2-imidazolin-2-yl)-5-methyl-nicotinic acid or salt thereof and is applied to the foliage or soil surrounding said turfgrasses at the rate of from 5.0 to 500.0 grams per hectare alone, or in combination with from 0.1 to 200.0 grams per hectare of another formula I imidazolinone compound or 20.0 to 500.0 grams per hectare of maleic hydrazide; and 20.0 to 500.0 grams per hectare of N-[2,4-dimethyl-5-[[(trifluoromethyl)sulfonyl]amino]phenyl]acetamide.

* * * * *